(12) United States Patent
Okubo et al.

(10) Patent No.: US 6,743,591 B1
(45) Date of Patent: Jun. 1, 2004

(54) METHOD FOR COUNTING LEUKOCYTES AND LEUKOCYTE COUNTER

(75) Inventors: Akio Okubo, Kyoto (JP); Shigeki Yamada, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 09/623,582

(22) PCT Filed: Mar. 11, 1999

(86) PCT No.: PCT/JP99/01202

§ 371 (c)(1),
(2), (4) Date: Aug. 31, 2000

(87) PCT Pub. No.: WO99/46599

PCT Pub. Date: Sep. 16, 1999

(30) Foreign Application Priority Data

Mar. 13, 1998 (JP) .............................................. 10-63589

(51) Int. Cl.$^7$ ...................... G01N 33/53; G01N 33/546
(52) U.S. Cl. .............................. 435/7.1; 435/4; 435/7.2; 435/7.21; 435/7.24; 435/7.72; 435/7.92; 435/28; 435/173.7; 435/173.5; 436/522; 436/523; 436/528; 436/529; 436/533; 436/534; 436/536; 436/545; 436/546; 436/63; 436/164; 436/165; 436/166
(58) Field of Search ........................... 435/2, 4, 7.1, 7.2, 435/6, 7.4, 7.21, 7.23, 7.24, 7.25, 7.72, 7.9, 7.92, 7.93, 7.94, 23, 24, 28, 173.4, 173.5, 173.7, 287.1; 436/523, 536, 524, 538, 529, 546, 532, 56, 533, 63, 534, 808, 522, 545, 164, 165, 166

(56) References Cited

U.S. PATENT DOCUMENTS

| 4,240,751 A | * | 12/1980 | Linnecke et al. ........... 356/409 |
| 5,096,808 A | * | 3/1992 | Harris ........................... 435/6 |
| 5,290,679 A | * | 3/1994 | Terao et al. .................. 435/7.4 |
| 5,464,739 A | | 11/1995 | Johnson et al. ................ 435/4 |
| 5,811,525 A | * | 9/1998 | Rittershaus ............ 530/388.22 |
| 6,024,918 A | * | 2/2000 | Hendricks et al. ............. 422/44 |

FOREIGN PATENT DOCUMENTS

| EP | 0519 720 | 6/1992 |
| EP | 0 661 280 | 12/1994 |

OTHER PUBLICATIONS

Jochum M; Granulocyte elastase as a sensitive diagnostic parameter of silent male genital tract inflammation. ANDROLOGIA, (Jul.–Aug. 1986) 18 (4) 413–9 (Abstract).*

(List continued on next page.)

*Primary Examiner*—Christopher L. Chin
*Assistant Examiner*—Gailene R. Gabel
(74) *Attorney, Agent, or Firm*—Merchant & Gould, P.C.

(57) ABSTRACT

A method for counting leukocytes which comprises liberating elastase from granulocytes contained in a specimen, adding an anti-granulocyte elastase antibody to the thus liberated elastase, measuring the antibody bonded to the elastase to thereby determine the concentration of the elastase, and then calculating therefrom the number of leukocytes contained in the specimen with the use of the ratio of the leukocyte count to the elastase concentration. This method makes it possible to conveniently and less expensively count leukocytes at a high accuracy comparable to the one established by using a conventional automatic blood cell counter, as the figure shows.

13 Claims, 1 Drawing Sheet

OTHER PUBLICATIONS

Ochnio et al., A sensitive double–sandwich ELISA for neutrophil elastase, American Review of Respiratory Disease 143 (1): 61–65 (Jan. 1991).*

Hafner et al., Evaluation of a new assay for the determination of PMN elastase– alpha proteinase inhibitor complexes in EDTA and citrated plasma, Clinical Laboratory, 43 (1–2): 3–9 (1997), Abstract Only.*

Ralfkiaer et al., Diagnosis of acute myeloid leukemia with the use of moniclonal anti–neutrophil elastase (NP57) reactive with routinely processed biopsy samples, Histology 14(6): 637–643 (Jun. 1989).*

Meier et al., Release of elastase from purified human lung mast cells and basophils, Inflammation 13(3): 295–308 (Jun. 1989).*

"Granulocyte Elastase as a Sensitive Diagnostic Parameter of Silent Male Genital Tract Inflammation", M. Jochum et al., Department of Clinical Chemistry and Clinical Biochemistry in he Surgical Clinic City, University of Munich, FRG and Department of Dermatology, Andrology Unit, University of Munich, FRG., Andrologia 18 (4): 413–419 (1986).

Hafner et al. "Determination of Human Granulocyte Elastase by the Immunoactivation Method on the Hitachi® 717 Automated Analyser" Eur. J. Clin. Chem. Clin. Biochem. vol. 29, 1991, pp 179–783.

European Search Report.

International Search Report.

* cited by examiner

METHOD FOR COUNTING LEUKOCYTES AND LEUKOCYTE COUNTER

TECHNICAL FIELD

The present invention relates to a method for counting leukocytes contained in a specimen and to a leukocyte counter used therefor.

BACKGROUND ART

In a blood test, blood cell counting is frequently carried out and its clinical significance is great. For example, an erythrocyte count permits examining the presence and the degree of anemia and further permits clinical diagnosis of various cases caused by oxygen deficiency in the tissue. On the other hand, a leukocyte plays an important role in a defense function of fighting bacteria or virus entering the body, namely, an immunological function. In particular, granulocytes or leukocytes have a function of liberating protease such as elastase, etc. by the stimulation of bacteria or foreign proteins entering the body, and a function of allowing elastase etc., to respond to the bacteria or foreign proteins. Since the leukocyte count is increased or decreased in the case of many diseases, it is important to count leukocytes in a screening for diseases. In diseases requiring an early determination or cure, the leukocyte count is a particularly important examination item. Furthermore, since the leukocyte count fluctuates in accordance with ages of subjects, daytime or night-time, seasons, and other factors, the leukocyte count is therefore desired to be determined in routine medical treatments appropriately and accurately.

At present, methods for counting blood cells crudely classified into two types, i.e., a visual counting method and an automatic counting method. In the visual counting method, blood cells are counted by microscopic examination on a calculating board. The visual counting method includes a technique for counting blood cells without any treatment and a technique for counting blood cells after staining nuclei of blood cells with dye. In the automatic counting method, blood is diluted to a certain amount and then allowed to pass through a thin flow passage so as to detect and count blood cells by using electrical resistance or scattered light. In this method, a specific blood cell counter is generally used. In these counting methods, blood cells themselves are counted either by human eyes or by using a counter. However, these methods have the below mentioned problems.

DISCLOSURE OF THE INVENTION

In the above-mentioned visual counting method, errors in counting occur regarding the kind of cells. Such errors can be caused by erythrocytes being deficient in hemolysis or the hemagglutination of blood cells, by homogeneous broadening of leukocytes on the calculating board, or the skill of laboratory technicians. Furthermore, in the visible counting method, a nucleated cell other than a leukocyte, for example, an erythroblast cell, etc. is counted as a leukocyte. Therefore, when a nucleated cell other than a leukocyte is present in peripheral blood, it is necessary to analyze the ratio of leukocytes to the other cells by using a blood smear preparation and to correct the value counted. Moreover, the visual counting method is a manual method, and therefore it takes a long time to count cells.

In the automatic counting method, the exact counted value may not be obtained because of the appearance of erythroblast cells, deposition of fibrin, platelet agglutination, deficiency in hemolysis of erythrocytes, and the like. Moreover, some measurement devices permit classifying the counted cells by a grain size distribution measurement function or a pattern recognition. Such devices make it possible to detect diseases easily. However, such devices are expensive and large. Not only such special devices but also general devices used for counting blood cells in the automatic counting method are large and expensive. Furthermore, the maintenance is complicated, for example, cleaning of a liquid flow passage, etc. is complex. Therefore, such devices are effective for such institutes as laboratories in large-scaled hospitals or examination centers, etc., which deal with a large number of specimens. However, for medium size hospitals or practitioners, etc. that deal with a small number of specimens, the use and the maintenance of the large-size device is a heavy burden.

Therefore, objects of the present invention are a method for counting leukocytes accurately and conveniently by using a small-size and inexpensive device, and a leukocyte counter used therefor.

In order to achieve the above-mentioned object, a method for counting leukocytes of the present invention includes: liberating elastase from neutrophils, eosionphils and basophils (hereafter, these three blood cells are referred to as "granulocytes") contained in a specimen; adding an anti-granulocyte elastase antibody to the thus liberated elastase; measuring the antigranulocyte elastase antibody bonded to the elastase to thereby determine the concentration of the elastase; and calculating the number of leukocytes contained in the specimen from the thus determined concentration of elastase by using a known ratio of the leukocyte count, the granulocyte count or the neutrophil count to the concentration of elastase.

Thus, the counting method of the present invention is a method for indirectly calculating the number of leukocytes by measuring the concentration of elastase contained in the granulocytes instead of actually counting leukocytes.

There are five classes of leukocytes, i.e., neutrophils, eosinophils, basophils, monocytes and lymphocytes. Three cells, i.e. neutrophils, eosinophils, basophils in all are called granulocytes. Moreover, the leukocyte count and the percentage of each class of leukocyte (a differential leukocyte count) in blood are not different between sexes and are substantially constant, although the percentage of each class of leukocyte is somewhat different between children and aged people. For example, in adult blood, the leukocyte count is about 6700 cells/$\mu$l and the average percentage of each class of leukocyte is; neutrophil 55.3%, eosinophil 3.5%, basophil 0.5%, monocyte 5.0% and lymphocyte 36.6%. Furthermore, the granulocyte is the largest in number among leukocytes and contains a large amount of elastase inside. Granulocyte elastase is liberated when the granulocyte is exposed to stimulation or damage by phagocytes or inflammation, thus responding to lesion. In blood, the above-mentioned elastase is present in its deactivated state by bonding to a protease inhibitor such as $\alpha$1-antitrypsin, or the like. The average retention time in blood is about 10 hours. Once the elastase is excreted into the tissue or urine, it does not return to the circulating blood again. Furthermore, the elastase concentration in the plasma is generally about one-several hundredth of the elastase concentration in granulocyte and is substantially negligible. The granulocyte elastase is different from elastase derived from the pancreas and an antibody for the granulocyte elastase does not cross-react with the elastase derived from the pancreas. The present invention uses such principles. More specifically, granulocytes are lysed so as to liberate the elastase from the granulocyte, and then the concentration of the liberated elastase is measured by an immunological technique. Consequently, even if the specimen is blood, the concentration can be measured exactly. From the measurement value, the number of leukocytes in the specimen can be calculated based on a known ratio of the leukocyte count, etc. to the elastase concentration. Thus, since the leukocytes are counted by using the concentration of elastase in granulocytes, the counting method is not affected by a nucleated cell other than a leukocyte, for example, an erythroblast cell, etc.; the deposition of fibrin; platelet agglutination; and deficiency in hemolysis of erythrocytes. Furthermore, the counter used for the method can be miniaturized, the cost for counting can be reduced and furthermore the counted value is not affected by the skill of laboratory technician because immunological techniques are used.

In the present invention, the leukocytes denote both individual leukocytes, i.e. neutrophils, eosinophils, basophils, monocytes and lymphocytes, and the whole population of leukocytes. Therefore, in the present invention, the number of individual blood cells constituting leukocytes, such as granulocytes including neutrophils, eosinophils and basophils, etc. may be counted, and the number of the entire population of leukocytes may be counted.

It is preferable that the method of the present invention includes bonding the same protease inhibitor as a protease inhibitor contained in the specimen to the liberated elastase, and then adding an antigranulocyte elastase antibody into the specimen. With such a preferable embodiment, when a protease inhibitor is contained in the specimen such as blood etc., the effect of the protease inhibitor can be eliminated. Therefore, it is preferable that when the specimen is whole blood, the protease inhibitor is $\alpha$1-antitrypsin, because $\alpha$1-antitrypsin is present in the largest amount (about 90%) among the protease inhibitors in blood.

In the counting method of the present invention, it is preferable that a latex agglutination immunoassay be employed as the immunological technique. More specifically, it is preferable that the method of the present invention includes causing an antigen-antibody reaction between an antibody particle in which the antigranulocyte elastase antibody is bonded to a latex particle and the elastase liberated from granulocytes, and determining the degree of agglutination of the latex particle to thereby measure the antigranulocyte elastase antibody bonded to the elastase. The latex agglutination immunoassay is preferred because it is a homogeneous immunoassay in which an antigen-antibody reaction is fast, and a bound/free (B/F) separation is not required, and therefore, it includes only a few steps so as to be carried out conveniently and at low cost. In addition, the method of the present invention includes bonding the elastase liberated from granulocytes to the antigranulocyte elastase antibody bonded to a solid phase; adding a labeled antigranulocyte elastase antibody therein in this state; and measuring the labeled antigranulocyte elastase antibody bonded to the elastase. Depending upon the labels, the immunological technique may be an enzyme immunoassay, a radioimmunoassay, a fluorescence immunoassay, and the like.

In the counting method of the present invention, as the known ratios, for example, the following first and second ratios are preferably used.

The first ratio is a statistical ratio of the leukocyte count or the granulocyte count to the elastase concentration. This statistical ratio includes, for example, a regression linear expression, etc. obtained by separately measured values of the elastase concentration and the number of leukocytes, etc. in the specimen such as blood. The regression linear expression includes a regression linear expression between the elastase concentration and the granulocyte count, a regression linear expression between the elastase concentration and the number of whole leukocytes, and the like.

The second ratio is the elastase concentration with respect to one granulocyte cell. From this ratio, the number of granulocytes contained in the specimen can be calculated. The elastase concentration with respect to one granulocyte cell is generally 1 to 5 ng/ml, preferably 2 to 2.5 ng/ml. Therefore, the number of whole leukocytes in the specimen may be calculated from the number of granulocytes by using a known ratio of a granulocyte count to the number of whole leukocytes.

Moreover, as the known ratio of the leukocyte count to the elastase concentration of the present invention, the conventionally known ratio may be used, or a ratio that was calculated in advance in accordance with the kinds of specimen may be used. Furthermore, the counting of leukocytes may be carried out by either the above-mentioned visual method or the automatic counting method. Also, the method for measuring the elastase concentration is not particularly limited, however, it is preferable to use the immunological techniques employed in the present invention.

Next, the leukocyte counter of the present invention is used for performing the method for counting leukocytes according to the present invention and the method includes a means for calculating the number of leukocytes in a specimen from the concentration of elastase liberated from granulocytes in the specimen by using a known ratio of a leukocyte count, a granulocyte count or a neutrophil count to a concentration of elastase.

It is preferable that the above-mentioned leukocyte counter includes a means for liberating elastase from granulocytes in the specimen, a means for adding an antigranulocyte elastase antibody to the thus liberated elastase, a means for measuring the antigranulocyte elastase antibody bonded to the elastase to thereby determine the concentration of elastase; and a means for calculating the number of leukocytes contained in the specimen from the determined concentration of elastase by using a known ratio of a leukocyte count, a granulocyte count or a neutrophil count to the concentration of elastase.

Next, the reagent kit of the present invention is used for performing the method for counting leukocytes according to the present invention and the kit includes an antigranulocyte elastase antibody.

The reagent kit of the present invention used for the method for counting leukocytes employing the latex agglutination immunoassay of the present invention includes an antibody particle in which an antigranulocyte elastase antibody is bonded to a latex particle.

The reagent kit used for the counting method of the present invention using a labeled antibody has an antigranulocyte elastase antibody bonded to a labeled antigranulocyte elastase antibody and to a solid phase. It is preferable that the labeled antigranulocyte elastase antibody is an enzyme-labeled antigranulocyte elastase antibody.

It is preferable that the reagent kit of the present invention includes the same protease inhibitor as the protease inhibitor contained in a specimen to be determined. Furthermore, when the subject specimen is whole blood, the protease inhibitor is preferably an $\alpha$1-antitrypsin. Furthermore, the reagent kit of the present invention includes a lysing substance.

BEST MODE FOR CARRYING OUT THE INVENTION

Figure 1:
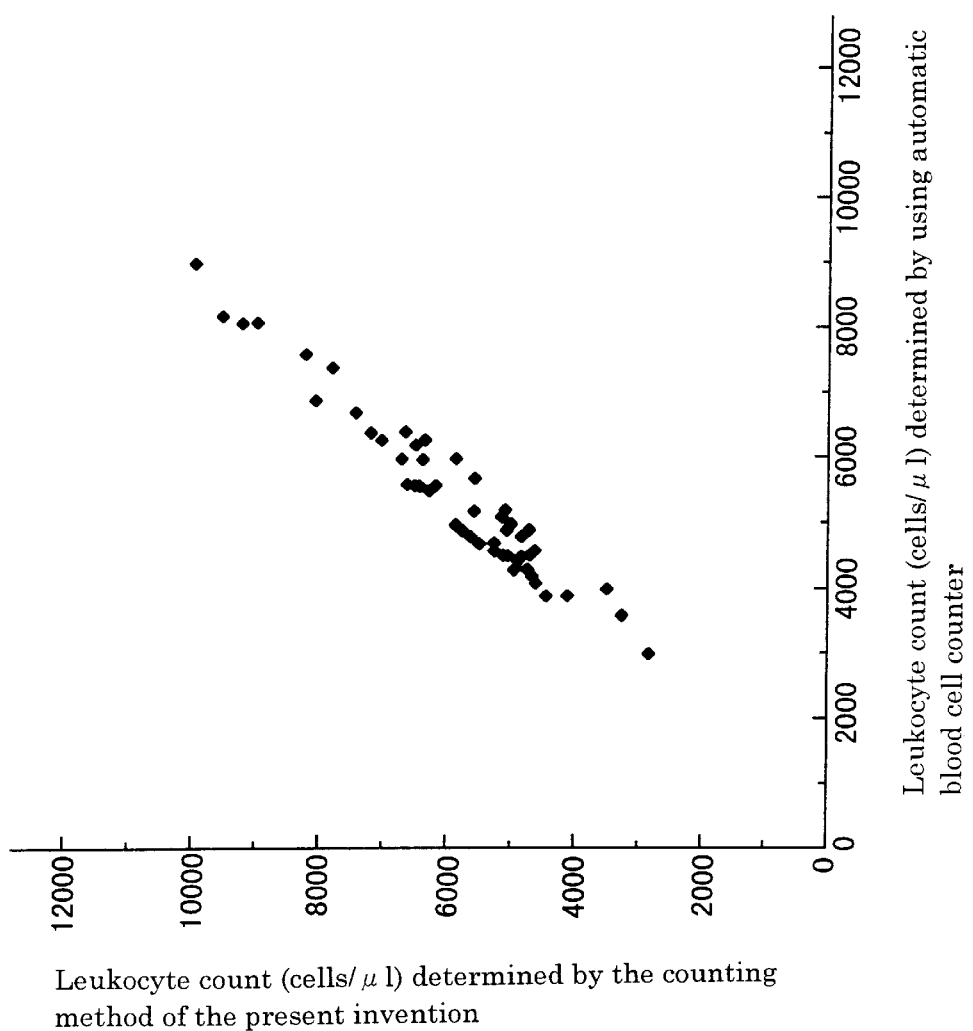
FIG. 1 is a graph showing the relationship between the leukocyte count determined by the counting method of the present invention and the leukocyte count determined by using an automatic blood cell counter in one embodiment of the present invention.

In the counting method of the present invention, first, granulocytes are lysed. The lysing method is not particularly limited and the conventionally known methods can be employed. Examples of such methods include a physical method using ultrasonic waves, etc., a method using the difference in the osmotic pressure, a chemical method using a surface active agent, etc., and the like. Above all, from the viewpoint of the operability etc., a method of immersing a specimen in an aqueous solution of a surface active agent is preferred. Examples of the surface active agent include dodecyltrimethylammonium bromide, dodecyltrimethylammonium chloride, saponin, lecithin, cholic acid , sodium dodecyl sulfate, 3-[(cholic amide propyl)dimethyl amino]-2-hydroxy-1-propanesulfonic acid, polyoxyethylene octylphenyl ether, polyoxyethylene sorbitol ester, and the like. The concentration of the active surface agent is not particularly limited and it is generally 0.001 to 5 weight %, preferably 0.05 to 1 weight Next, the elastase liberated from granulocytes is measured by an immunological technique.

Moreover, as mentioned above, it is preferable that when the specimen is whole blood, prior to this measurement, a protease inhibitor is added to the specimen in order to form the free-state elastase liberated from the granulocytes into a complex of the protease and the elastase. It is because the elastase liberated from the granulocytes is in a free state and exists as a complex that is bonded to the protease inhibitor in the plasma and because a subject to be measured is preferably a complex. Examples of the protease inhibitor include, in addition to α1-antitrypsin, α2-macroglobulin, and the like. Furthermore, the adding rate of the protease inhibitor is appropriately decided depending upon the concentration of the specimen, and the like, however, it is generally 5 to 10 times, preferably 8 to 12 times the weight with respect to the weight of granulocyte elastase.

As the immunological technique mentioned above, there are, for example, the latex agglutination immunoassay, the enzyme immunoassay, a radioimmunoassay, the fluorescent immunoassay, and the like.

The antigranulocyte elastase antibody used in the present invention can be prepared from the blood serum of an animal immunized with granulocyte elastase by conventional methods. Furthermore, it can also be prepared by conventional hybridoma methods. The animal used for preparing antibody includes, for example, sheep, rabbit, etc. However, the present invention is not limited to them.

The latex agglutination method uses an antigranulocyte elastase antibody bonded to latex particles. This method determines the elastase concentration by measuring the degree of the agglutination without performing B/F separation, because the latex particles are agglutinated, and thus a B/F separation is not required. In the determination of the agglutination degree, a spectrophotometer is generally used and the transmitted light is determined as turbidity. As the agglutination degree is increased, scattered light is increased to thereby reduce the transmitted light and the turbidity is enhanced. Moreover, the measurement wavelength is generally 400 to 1500 nm, preferably 500 to 800 nm. Furthermore, the adding rate of the antigranulocyte elastase antibody bonded to latex particles is appropriately decided in accordance with the kinds of specimens or the concentration, etc. When the specimen is whole blood, the adding rate is generally 0.1 to 5 mg/ml, preferably 1 to 3 mg/ml. Furthermore, the agglutination degree may be determined by using nephelometry. Furthermore, the agglutination degree may be determined visually. In this case, the use of commercially available reagents for the visual determination permits the highly accurate determination.

The antigranulocyte elastase antibody bonded to latex particles can be prepared by conventional methods. For example, antibody may be physically adsorbed or covalently-bonded to latex particles at the rate of 200 ng/cm$^2$. The latex particles have an average particle size of 0.1 to 0.2 μm and include polyethylene that is graft-copolymerized to polystyrene. Moreover, as the antigranulocyte elastase antibody bonded to latex particles, commercially available products may be used.

As mentioned above, the enzyme immunoassay includes: first, bonding elastase liberated from granulocytes to an antigranulocyte elastase antibody that is immobilized on a solid phase; further adding antigranulocyte elastase antibody labeled with an enzyme; separating the unbound antibody by means washing, etc.; and measuring the enzyme-labeled antigranulocyte elastase antibody bonded to the elastase by the reaction between the enzyme and its substrate.

As the combination of enzyme and substrate, a combination capable of producing detectable products by a reaction between the enzyme and the substrate is preferred. Examples of combinations include a combination of peroxidase, hydrogen peroxide and orthophenylene diamine, and a combination of alkaline phosphatase and 4-nitrophenyl phosphate. In a case where the combination of peroxidase, hydrogen peroxide and orthophenylene diamine is used, orthophenylene diamine develops color by the enzymatic reaction. The color is assayed at the wavelength of 492 nm.

The antibody immobilized on the solid phase can be prepared by conventional methods. For example, the antibody can be immobilized on the solid phase by an acid treatment, a heat treatment, and the like. Furthermore, the enzyme-labeled antibody can be prepared by conventional methods. For these antibodies, commercial products may be used.

Furthermore, the amount of the immobilized antibody and the addition rate of the enzyme-labeled antibody can be decided appropriately in accordance with the kinds of specimens, the concentration, and the like. Examples of the solid phase include a bead surface, tube surface, and the like.

The radioimmunoassay uses an antigranulocyte elastase antibody labeled with a radioactive substance instead of an enzyme. The radioimmunoassay is carried out in the same way as the enzyme immunoassay except that the radioactive substances are assayed. An example of the radioactive substance includes 126I-Na.

The fluorescent immunoassay uses an antigranulocyte elastase antibody labeled with a fluorescent substance instead of an enzyme. The fluorescent immunoassay is carried out in the same way as the enzyme immunoassay except that the fluorescent substances are assayed. Examples of the fluorescent substance include rhodamine, fluorescein, coumarin, and the like.

Next, from the concentration of elastase obtained by the above-mentioned immunological techniques, the number of leukocytes in the specimen is calculated by using a known ratio of the leukocyte count to the concentration of granulocyte elastase. As the known ratio, for example, the statistic ratio or the concentration of elastase to one granulocyte cell can be used. Furthermore, it is preferable that the ratio is decided appropriately in accordance with the kinds of specimens. For example, when the specimen is whole blood of adult, whole blood of child or whole blood of aged person, respective ratios may be used.

Next, it is preferable that the leukocyte counter of the present invention includes a means for liberating elastase from granulocytes in the specimen, a means for adding an antigranulocyte elastase antibody to the thus liberated elastase, a means for measuring the antigranulocyte elastase antibody bonded to the elastase to determine the concentration of elastase; and a means for calculating the number of leukocytes contained in the specimen from the determined concentration of elastase by using a known ratio of a leukocyte count, a granulocyte count or a neutrophil count to the concentration of elastase. With this counter, the number of leukocytes can be calculated fully automatically.

The means for liberating elastase and means for adding the antibody include elements such as a pump for divided injection etc. of the reagent, a valve, a nozzle, a stirrer, a container, a mechanism for adjusting temperature, etc. Furthermore, the means for measuring the elastase concentration includes, for example, an optical measurement system, etc. in addition to the above-mentioned elements. Furthermore, the calculating means includes, for example, a calculating mechanism programmed so that the number of granulocytes or the number of whole leukocytes in the specimen can be calculated from the elastase concentration and the above-mentioned known ratio, and a mechanism (display, printer, etc.) for displaying the calculated results.

In this way, the counter for performing the counting method of the present invention also can be made to be the same size as A4 size paper. The counter of the present invention is extremely small and inexpensive as compared with that of the conventional automatic counting method.

The counter for counting leukocytes of the present invention has at least a means for calculating the number of leukocytes from the concentration of elastase liberated from granulocytes in the specimen by using the known ratio of a leukocyte count, a granulocyte count or a neutrophil count and the elastase concentration. Other means are not always necessary. For example, the reagent or antibody may be added by hand. Furthermore, the elastase concentration may be measured by using the optical measuring system or may be measured visually.

Next, as the reagent kit of the present invention, the reagents exemplified in the counting methods can be used.

Hereinafter, the present invention will be described by way of examples and comparative examples.

EXAMPLE 1

Specimen was prepared by diluting adult whole blood with phosphate buffered saline (pH 7.4) into various concentrations (5 types). Each of these specimens was added to 0.1 weight % aqueous solution of dodecyltrimethylammonium chloride so as to lyse leukocytes. Each of the specimens was diluted with 0.01 weight % of polyoxyethylene sorbitol ester containing α1-antitrypsin so as to prepare a plurality of test liquids. The elastase concentration of 100 μl of each test liquid was measured by the above-mentioned technique (the enzyme immunoassay) by using an immobilized antibody (antihuman granulocyte elastase mouse monoclonal antibody) and an enzyme-labeled antibody (peroxidase-labeled antihuman granulocyte elastase sheep polyclonal antibody).

First, 100 μl of each test liquid was added to the immobilized antibody in a reaction solution and washed. Then, the enzyme-labeled antibody was added and washed. Finally, hydrogen peroxide and orthphenylene diamine were added to the reaction solution. Color developed by the enzyme reaction was determined by the absorbance at the wavelength of 492 nm and the elastase concentration was calculated by using a calibration curve that had been made in advance.

A regression linear expression between the number of leukocytes and the elastase concentration was formed with respect to another adult whole blood sample. The number of leukocytes was counted by using an automatic blood cell counter (K-4500 produced by TOA MEDICAL ELECTRONICS CO., LTD.). The concentration of granulocyte elastase was measured in the same way as the above-mentioned enzyme immunoassay. This regression linear expression (1) is shown below. The number of leukocytes in each specimen was calculated from the concentration of elastase by using this regression linear expression (1). Table 1 shows the results.

$$Y = 2132.9897x \square 0245.6519 \qquad (1)$$

X: concentration of granulocyte elastase (μg/ml)

Y: number of whole leukocytes (cell/μl)

As a control, the number of leukocytes in each specimen was counted by using the automatic blood cell counter (K-4500 produced by TOA MEDICAL ELECTRONICS CO., LTD.). The results are also shown in Table 1.

EXAMPLE 2

The number of whole leukocytes was calculated by using the elastase concentration with respect to one neutrophil cell, i.e., 0.9084 ng/ml and the ratio of the neutrophil count to the number of the whole leukocytes, i.e., 55.3%. The determination of the elastase concentration with respect to one neutrophil cell was calculated from only neutrophils counted by the usual method (the visual method) and the elastase concentration measured by the same technique as Example 1 (the enzyme immunoassay) except that a regression linear expression in Example 1 was not used. Table 2 shows the results.

COMPARATIVE EXAMPLE

Five kinds of test liquid were prepared the same way as in Example 1. 10 μl of each test liquid was added to 250 μl of Good's buffer solution (HEPES, pH7.5) and incubated at 37° C. for 3 minutes. To this test liquid, 4 mg/ml of aqueous solution of AAPV (methoxysuccinyl-Ala-Ala-Pro-Val-nitroanalide) was added, stirred and incubated at 37° C. for 6 minutes. Thereafter, the absorbance of the reaction solution was measured at the wavelength of 405 nm and the elastase activity was determined. Furthermore, as a control, similar to Example 1, the number of whole leukocytes was counted by using the automatic blood cell counter (K-4500 produced by TOA MEDICAL ELECTRONICS CO., LTD.). Table 3 shows the results.

TABLE 1

Example 1

| Number of control leukocytes (cell/μl) | Elastase concentration (μg/ml) | Calculated number of leukocytes (cell/μl) |
|---|---|---|
| 1000 | 0.36 | 522 |
| 2100 | 1.51 | 2975 |
| 4200 | 2.02 | 4063 |
| 6300 | 2.99 | 6132 |
| 8400 | 4.01 | 8308 |

TBLE 2

Example 2

| Number of control leukocytes (cell/μl) | Elastase concentration (μg/ml) | Calculated number of leukocytes (cell/μl) |
|---|---|---|
| 1000 | 0.36 | 717 |
| 2100 | 1.51 | 3006 |
| 4200 | 2.02 | 4021 |
| 6300 | 2.99 | 5952 |
| 8400 | 4.01 | 7983 |

TABLE 3

Comparative Example

| Number of control leukocytes (cell/μl) | Elastase activity (U/ml) |
|---|---|
| 730 | 4.3 |
| 1090 | 24.8 |
| 1540 | 7.8 |
| 1970 | 52.8 |
| 2670 | 33.4 |

As shown in Tables 1 and 2, in Examples 1 and 2, the number of whole leukocytes calculated from the elastase concentration and the number of whole leukocytes counted by using the automatic blood cell counter were highly correlated (correlation coefficient r=0.986). On the other hand, in the comparative example, the correlation between the elastase concentration (the enzyme activity) and the number of whole leukocyte counted by using the automatic blood cell counter was low (correlation coefficient r=0.6268). This is thought to be because in the comparative example, the activity of elastase was inhibited by the protease inhibitor (α1-antitrypsin, etc.) in the specimen with the result that the elastase concentration was measured by the enzyme immunoassay.

EXAMPLE 3

Five kinds of specimens were prepared the same way as in Example 1. The elastase concentration of each of these 5 specimens was measured by the below mentioned latex agglutination immunoassay. More specifically, first, each of the above-mentioned specimens was added to 0.1 weight % of saponin aqueous solution so as to lyse leukocyte. This was diluted in the same way as in Example 1 to prepare test liquid. 10 μl of this test liquid was added to 250 μl of phosphate buffered saline (pH7.4), then 50 μl of latex suspension (concentration: 2.0 mg/ml), which had been sensitized by antihuman granulocyte elastase antibody, was added to the test liquid, and incubated at 37° C. for 15 minutes. The latex suspension was prepared by physically adsorbing the above-mentioned antibody to the latex particles, which have an average particle size of 0.1 to 0.2 μm and in which polyethylene was graft-copolymerized to polystyrene at the rate of about 200 ng/cm$^2$. Then, the absorbance (turbidity) of this buffer solution was determined at the wavelength of 660 nm by using a spectrophotometer and the elastase concentration was measured. From the numeral value, the number of leukocytes in the specimen was calculated in the same way as in Example 1. Furthermore, as a control, the number of leukocytes in each specimen was counted by using the automatic blood cell counter (K-4500, TOA MEDICAL ELECTRONICS CO., LTE. ). Table 4 shows the results.

TABLE 4

Example 3

| Dilution level of specimen | Number of control leukocytes (cell/μl) | Elastase concentration (μg/ml) | Calculated number of leukocytes (cell/μl) |
|---|---|---|---|
| 1/16 | 1100 | 0.40 | 1284 |
| 1/8 | 1600 | 1.70 | 1996 |
| 1/4 | 3300 | 3.04 | 2766 |
| 1/2 | 6600 | 9.53 | 6498 |
| 1 | 13200 | 21.32 | 13277 |

As shown in Table 4, in Example 3, the number of leukocytes calculated from the elastase concentration and the number of whole leukocytes counted by using the automatic blood cell analyzer were highly correlated (correlation coefficient r=0.998).

EXAMPLE 4

The number of leukocytes in the specimen was calculated in the same way as in Example 3 by using 50 cases of adult whole blood (n=50) as the specimens. Furthermore, as controls, the number of leukocytes of each of the above-mentioned specimens (n=50) was counted by using the automatic blood cell counter (K-4500 produced by TOA MEDICAL ELECTRONICS CO., LTD.). FIG. 1 shows the results. FIG. 1 is a graph showing the relationship between the number of leukocytes counted by the counting method according to the present invention and the number of leukocytes counted by using the automatic blood cell counter concerned in each specification (n=50).

As shown in FIG. 1, in each specimen (n=50), the number of leukocytes calculated from the elastase concentration and the number of whole leukocytes counted by using the automated analyzer were highly correlated (correlation coefficient r=0.973).

Industrial Applicability

As mentioned above, according to the method for counting leukocytes of the present invention, the number of leukocytes in a specimen was calculated from the concentration of elastase contained in granulocytes, which was measured by the immunological technique. With this method, leukocytes can be counted without being affected by nucleated cells other than leukocytes, for example, erythroblast cells, etc., deposition of fibrin, platelet agglutination, and deficiency in hemolysis of erythrocytes. Furthermore, the counter can be miniaturized and the counting cost can be reduced according to the method of the present invention. Furthermore, since this method uses the immunological technique, it is not influenced by the skill of laboratory technicians.

What is claimed is:

1. A method for counting granulocytes, wherein granulocytes encompass neutrophils, eosinophils and basophils, the method comprising:
   liberating elastase from granulocytes contained in a specimen by lysing the granulocytes;
   adding an antigranulocyte elastase antibody to the liberated elastase to bind the elastase;
   measuring the antigranulocyte elastase antibody bound to the elastase to thereby determine the concentration of the elastase; and
   calculating the number of granulocytes contained in the specimen from the determined concentration of elastase using a known ratio of granulocyte count or neutrophil count to elastase concentration.

2. The method according to claim 1, further comprising: binding a protease inhibitor to the liberated elastase, before adding the antigranulocyte elastase antibody to the elastase, wherein the protease inhibitor is endogenous to the specimen.

3. The method according to claim 2, wherein the specimen is whole blood and the protease inhibitor is α1-antitrypsin.

4. The method according to claim 2, wherein the protease inhibitor is added in the range from 5 to 10 times weight as compared to a known weight of granulocyte elastase.

5. The method according to claim 1, wherein the step of adding an antigranulocyte elastase antibody to the liberated elastase comprises adding antigranulocyte elastase antibody immobilized on latex particles to the elastase liberated from granulocytes, and allowing an antigen-antibody binding reaction to occur, and wherein the step of measuring the antigranulocyte elastase antibody bound to the elastase comprises determining the degree of agglutination of the latex particles.

6. The method according to claim 5, wherein the antigranulocyte elastase antibody immobilized on latex particles are added at the rate of 0.1 to 5 mg per 1 ml of the specimen.

7. The method according to claim 1, wherein the step of binding the elastase liberated from granulocytes to the antigranulocyte elastase antibody comprises immobilizing the antibody on a solid phase; adding the specimen containing liberated elastase; adding a labeled antigranulocyte elastase antibody; and measuring the labeled antigranulocyte elastase antibody bound to the elastase.

8. The method according to claim 7, wherein the label on the labeled antigranulocyte elastase antibody is an enzyme label, a radioactive label, or a fluorescent label.

9. The method according to claim 7, wherein the label on the labeled antigranulocyte elastase antibody is an enzyme and a detectable product is produced by a reaction between the enzyme and its substrate; wherein the method further comprises the step of adding the substrate before the measuring step.

10. The method according to claim 9, wherein the enzyme is peroxidase and its substrate is orthophenylene diamine and hydrogen peroxide.

11. The method according to claim 1, wherein the known ratio is a statistical ratio of a granulocyte count to a corresponding elastase concentration.

12. The method according to claim 1, wherein the known ratio is an elastase concentration of one granulocyte cell.

13. The method according claim 12, wherein the elastase concentration of one granulocyte cell is in the range of from 1 to 5 ng/ml.

* * * * *